US005763688A

United States Patent [19]
Ikariya et al.

[11] Patent Number: 5,763,688
[45] Date of Patent: Jun. 9, 1998

[54] METHOD FOR PRODUCING AN ALCOHOL

[75] Inventors: Takao Ikariya, Nagoya; Takeshi Ohkuma, Aichi-gun; Hirohito Ooka; Shohei Hashiguchi, both of Nagoya; Nobuo Seido, Yokohama; Ryoji Noyori, Nisshin, all of Japan

[73] Assignee: Research Development Corporation of Japan, Japan

[21] Appl. No.: 568,589

[22] Filed: Dec. 7, 1995

[30] Foreign Application Priority Data

Dec. 7, 1994 [JP] Japan ................ 6-304070
Dec. 7, 1994 [JP] Japan ................ 6-304071

[51] Int. Cl.$^6$ ................................ C07C 29/36
[52] U.S. Cl. ............... 568/814; 568/855; 568/861; 549/475; 549/70; 546/340; 544/242
[58] Field of Search ................ 568/814, 855, 568/861; 549/475; 449/70; 546/340; 544/242

[56] References Cited

U.S. PATENT DOCUMENTS

| | | |
|---|---|---|
| 3,527,817 | 9/1970 | Dietzler et al. .................. 260/618 |
| 4,290,961 | 9/1981 | Mestroni et al. ................. 260/397.4 |
| 5,066,815 | 11/1991 | Sayo et al. ...................... 549/319 |
| 5,227,538 | 7/1993 | Buchwald et al. ............... 568/814 |
| 5,254,752 | 10/1993 | Merger et al. ................... 568/812 |

OTHER PUBLICATIONS

Kazuhide Tani et al; Rh(I) complexes—carbonyl compounds; Chemistry Letters;pp. 261–264, 1982.

*Primary Examiner*—Gary Geist
*Assistant Examiner*—Sreeni Padmanabhan
*Attorney, Agent, or Firm*—Wenderoth, Lind & Ponack

[57] ABSTRACT

The present invention provides a method for producing a alcohol including an optically active alcohol by hydrogenating a carbonyl compound in the presence of a homogeneous catalyst, a base and a nitrogen-containing organic compound. Thus, the reaction employs an inexpensive catalyst and proceeds in high yield and high efficiency.

5 Claims, No Drawings

METHOD FOR PRODUCING AN ALCOHOL

FIELD OF THE INVENTION

The present invention relates to a method for producing an alcohol. More particularly, the present invention relates to a novel method for efficient production at a high yield of alcohol useful as medical drugs, agricultural chemicals, various other chemicals or raw material or a synthetic intermediate thereof, ant to a new method for producing optically active alcohol, which is excellent in practicability and useful in various uses including synthetic intermediates of medical drugs and material for liquid crystal.

PRIOR ART AND PROBLEMS

Method for producing alcohol have been conventionally known, which comprise hydrogenation of carbonyl compound, by using a homogeneous catalyst system, thereby obtaining corresponding alcohol, including fort example: (1) a method using a ruthenium complex as described in Comprehensive Organometallic Chemistry, Vol 4, p. 931 (1982), Eds. G.Wilkinson, F. G. A. Stone and E. W. Abel; (2) methods using a rhodium complex as described in Inorg. Nucl. Chem. Letters, Vol. 12, p. 865(1976); J. Organomet. Chem., Vol. 129, p. 239 (1997); Chem. Letters, P. 261 (1982); and Tetrahedron Letters, Vol 35, p, 4963 (1994); and (3) a method using an iridium complex as described in J. An. Chem. Soc., Vol. 115, p. 3318 (1993).

However, these conventional methods require as a catalyst any of such metals as ruthenium, rhodium, iridium, palladium and platinum which are relatively expensive nobel metals, and the metals have problems in that the hydrogenation activity is low and the reaction requires specific conditions including a relatively high temperature or a high hydrogen pressure, thus making these materials unsuitable for practical use.

Additionally, the conventionally known methods for asymmetrically synthesizing optically active alcohol include: 1) a method using an enzyme such as baker's yeast, and 2) a method for asymmetric hydrogenation of a carbonyl compound by the use of a metal complex catalyst. Particularly, regarding the latter method, many cases of asymmetric catalytic reactions have been reported, including for example: (1) a method of asymmetric hydrogenation of a carbonyl compound having a functional group using optically active ruthenium catalyst described in detail in Asymmetric Catalysis In Organic Synthesis, p. 56–82 (1994) ed. R. Noyori; (2) a method based on hydrogen transfer type reduction reaction through asymmetric complex catalysis of ruthenium, rhodium and iridium described in Chem. Rev., Vol. 92, p. 1051–1069 (1992); (3) a method of asymmetric hydrogenation using a nickel catalyst prepared by modifying tartaric acid described in Petr. Chem., p. 882–831 (1980) and Advances in Catalysis, Vol. 32, p. 215 (1983) ed. Y. Izumi; (4) a method based on asymmetric hydrosilation as described in Asymmetric Synthesis, vol 5, Chap. 4 (1985) ed. J. D. Morrison and J. Organomet. Chem., Vol. 346, p. 413–424 (1988); and a method of borane-reduction in the presence of chiral ligands described in J. Chem. Soc., Perkin Trans. 1, p. 2039–2044 (1985) and J. Am. Chem. Soc., Vol. 109, p. 5551–5553 (1987).

Although the method using an enzyme gives alcohol with a relatively high optical purity, however, it is defective in that kinds of reaction substrates are limited, and the resultant alcohol is limited to one having a specific absolute configuration. In the case of the method using an asymmetric hydrogenation catalyst based on a transition metal, while realizing production of optically active alcohol with a high selectivity for such a substrate as keto acid, for example, it has a drawback of a low reaction rate, and in addition, the method is not valid for relatively simple carbonyl compounds having no functional group in the molecule.

For these reasons, there has been a demand for achievement of a new synthetic method for producing an optically active alcohol having a high generality and using a highly active catalyst.

SUMMARY OF THE INVENTION

The present invention has therefore an object to solve these problem in the prior arts, and provide a novel method for producing an alcohol through a hydrogenation reaction with a high efficiency by the use of an inexpensive catalyst system.

As means to solve the above-mentioned problems, the present invention provides a method for producing an alcohol, which comprises the step of subjecting a carbonyl compound to a hydrogenation reaction in the presence of a homogeneous hydrogenation catalyst, a base, and a nitrogen-containing organic compound.

Particularly, in the present invention, a catalyst of a VIII-group metal complex is used as a catalyst of a higher activity. A base and a nitrogen-containing organic compound are also used in addition to the VIII-group metal complex.

As the carbonyl compound which is the raw material for producing an alcohol through hydrogenation reaction, for example, a compound expressed by the following formula (1):

(where, $R^1$ and $R^2$ are aromatic monocyclic or polycyclic hydrocarbon groups or hetero-monocyclic or polycyclic groups containing heteroatoms, which may have the same or different substitution groups or a saturated or unsaturated chain or cyclic hydrocarbon group, any one on which may be hydrogen atom. $R^1$ and $R^2$ also may form a cyclic group by themselves) may appropriately be used.

The present invention also provides a method for producing an optical active alcohol, which comprises the step of subjecting a carbonyl compound expressed by the following general formula (2):

(where, $R^3$ is an aromatic monocyclic or polycyclic hydrocarbon group, a saturated or unsaturated aliphatic or cyclo-hydrocarbon group, or a hetero-monocyclic or polycyclic group containing heteroatoms, which may have a substitution group $R^4$; and $R^4$ is a saturated or non-saturated chain, cyclic or aromatic cyclic hydrocarbon or heterocyclic group, which may have hydrogen or a substitution group. $R^3$ and $R^4$ also may form a cyclic groups by themselves.) to a hydrogenation reaction in the presence of an asymmetric hydrogenation catalyst of a transition metal, a base and a optically active nitrogen-containing compound thereby producing optically active alcohol expressed by the following general formula (3):

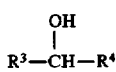

$$R^3-\overset{\overset{OH}{|}}{CH}-R^4 \quad (3)$$

(where, $R^3$ and $R^4$ are the same organic groups as above).

DETAILED DESCRIPTION OF THE INVENTION

Regarding the present invention for a method of producing an alcohol, the substitution group in the case of formula (1), any of various organic groups which never impairs hydrogenation reaction, such as hydrocarbon group, halogen group, hydroxy group, alkoxy group, carboxyl group, ester group, amino group and heterocyclic group may appropriately be used.

As $R^1$ and $R^2$, applicable ones include hydrogen atom; aromatic monocyclic or polycyclic groups such as phenyl group, 2-methylphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, cumenyl, mesityl, xylyl, 1-naphthyl, 2-naphthyl, anthryl, phenanthryl, and indenyl; heteromonocyclic or polycyclic groups such as thienyl, furyl, pyranyl, xanthenyl, pyridyl, pyrrolidyl, imidazolyl, indolyl, and phenanthrolyl; and ferrocenyl group, cyclic or acylic hydrocarbon groups, for example, alkyl groups such as methyl, ethyl, propyl, butyl, pentyl, hexyl, and heptyl, cycloalkyl groups such as cyclopropyl, cyclobutyl, cyclopentyl and cyclohexyl, and hydrocarbons containing unsaturated groups such as benzyl, vinyl and allyl.

In case of cyclic group formed by connecting $R^1$ and $R^2$, for example, saturated or unsaturated cyclo-aliphatic groups providing cyclic ketone such as cyclopentanone, cyclohexanone, cycloheptanone, cyclopentenone, cyclohexenone, cycloheptenone; substituted saturated or unsaturated cyclo-aliphatic groups having substitution groups selected from alkyl, aryl, unsaturated alkyl, aliphatic or cyclo-aliphatic group containing hetero atom; are mentioned.

The VIII-group metals include rhodium (Rh), ruthenium (Ru), iridium (Ir), palladium(Pd), and platinum(Pt). Particularly, ruthenium(Ru) is used for a high activity in the present invention for producing an alcohol.

These VIII-groups metals are used in the form of soluble complex catalyst as homogeneous catalyst. For example, this catalyst can be expressed by the following general formula (4).

$$MX_mL_n \quad (4)$$

(where, M is a VIII-group metal; X is halogen atom, carboxyl group, alkoxy group or hydroxy group; and L is phosphine, olefin, diolefin, cycloolefin, CO, arsine, amine or other organic ligand)

For example, phosphine ligand can be expressed by a general formula $PR^5R^6R^7$, where $R^5$, $R^6$, and $R^7$ may be the same or different, and are aliphatic groups, alicyclic groups or aromatic groups, or may be bidentate phosphine ligands. Applicable phosphine ligands include, for example, such tert-phosphines as trimethylphosphine, triethylphosphine, tributyl-phosphine, triphenylphosphine, tricyclohexylphosphine, tri(p-tolyl)phosphine, diphenylmethylphosphine, dimethylphenylphosphine, and bidentate tert-phosphine compounds such as bis-diphenylphosphinoethane, bis-diphenylphosphinopropane, bis-diphenylphosphinobutane, bis-dimethylphosphinoethane, and bis-dimethylphosphinopropane.

As complex based on ligand described above, preferable examples include complexes of ruthenium, rhodium, iridium, palladium and platinum. Among others, ruthenium complex has a high activity More specifically, applicable complexes include $RuCl_2[P(C_6H_5)_3]_4$, $RuCl_2[P(C_6H_5)_3]_3$, $RuH_2[P(C_6H_5)_3]_4$, $RuHCl[P(C_6H_5)_3]_4$, $RuH(HCOO)[P(C_6H_5)_3]_3$, $RuH(CH_3COO)[P(C_6H_5)_3]_3$, $RUCl_2[P(CH_3)(C_6H_5)_2]_4$, $RuCl_2[(C_6H_5)_2P(CH_2)_2P(C_6H_5)_2]_2$, $RuCl_2[P(CH_3)_3]_4$, $RuHCl[P(CH_3)_3]_4$, $RuBr_2[P(C_6H_5)_3]_4$, and $RuI_2[P(C_6H_5)_3]_4$. It is needless to mention that complexes applicable are not limited to those enumerated above.

The amount of the VIII-group transition metal complex for the method of production of an alcohol, varying with the reactor volume and economic merits, can be at a ratio within a range of from 1/100 to 1/100,000 in mole ratio, or more a range of from 1/100 to 1/100,000 in mole ratio, or more preferably, within a range of from 1/500 to 1/100,000 in mole ratio relative to the carbonyl compound which is the raction raw material.

Bases applicable in the present invention include inorganic and organic bases. In the bases expressed by the general formula MY, for example, M is an alkali metal or an alkaline earth metal, and Y is a hydroxy group, alkoxy group, mercapto group or naphthyl group, and more specifically, applicable ones include KOH, KOCH3, KOCH$(CH_3)_2$, $KC_{10}H_8$, $KOC(CH_3)_3$, LiOH, LiOCH$_3$, and LiOCH$(CH_3)_2$, NaOH, NaOCH$_3$, NaOCH$(CH_3)_2$ as well as quaternary ammonium salt.

The amount of the base as described above should be within a ragnge of from 0.5 to 10,000 equivalents, or more preferably, from 2 to 40 equivalents relative to the VIII-group transition metal complex.

As the nitrogen-containing organic compound used in the present invention, amine compounds are typical examples.

The amine compound may be a mono-amino comprising of primary amine, secondary-amine, or tertiary amine expressed by a general fomrmula $NR^8R^9R^{10}$, or a diamine expressed by a general formula $R^{11}R^{12}N-Z-NR^{13}R^{14}$.

In these formula, $R^8$, $R^9$, $R^{10}$, $R^{11}$, $R^{12}$, $R^{13}$ and $R^{14}$ indicate hydrogen, or the same or different ones selected from alkyl group, cycloalkyl group and aryl group having a carbon number within a range of from 1 to 10, and may include cyclic diamine Z is a group selected from alkyl group, cycloalkyl group and aryl group having a carbon number of from 1 to 6. Examples include mono amine compounds such as methylamine, ethylamine, propylamine, butylamine, pentylamine, hexylamine, cyclopentylamine, cyclohexylamine, benzylamine, dimethlyamine, diethylamine, dipropylamine, dihexylamine, dicylopentylamine, dicyclohexylamine, dibenzylamine, diphenylamine, phenylethylamine, piperidino and piperadine; and diamine compounds such as methylenediamine, ethylenediamine, 1,2-diaminopropane, 1,3-diaminopropane, 1,4-diaminobutane, 2,3-diaminobutane, 1,2-cyclopentanediamine, 1,2-cyclohexanediamine, N-methylethylenediamine, N,N'-dimethylethylenediamine, N,N,N'-trimethylethylenediamine, N,N,N',N'-tetramethylethylenediamine, o-phenylenediamine, and p-phenylenediamine.

The amount of these compounds should be within a range of from 1 to 1000 equivalents relative to the transition metal complex in the case of monoamine compound, or more preferably, from 2 to 4 equivalents, and within a range of from 0.5 to 2.5 equivalents in the case of diamine compound, or more preferably, from 1 to 2 equivalents.

The transition metal complex used as the catalyst, the base and the nitrogen-containing compound are indispensable for ensuring smooth progress of reaction. The absence of even any of these constituents makes it impossible to obtain a sufficient reaction activity.

In the present invention, furthermore, any liquid solvent which can dissolve the raction raw materials and catalyst constituents may be used. Applicable solvents include aromatic hydrocarbon solvents such as toluene and xylene, aliphatic hydrocarbon solvents such as pentane and hexane, halogen-containing hydrocarbon solvents such as metylene chloride, ether type solvents such as ether and tetrahydrofuran, alcohol type solvents such as methanol, ethanol, 2-propanol, butanol, benzyl alcohol, and organic solvents containing heteroatoms such as acetonitrile, DMF and DMSO. Since the product is alcohol, alcohol type solvents are preferable. More preferably, 2-propanol may be preferably used. When the reaction substrate is hardly soluble in a solvent, a mixed solvent comprising ones selected from those enumerated above may be used.

The amount of the solvent is determined from solubility of the reaction substrate and relative economic merits. In the case of 2-propanol, the reaction may be caused at a substrate concentration within a range of from a low concentration of under 1% to a state near the non-existence of solvent, but it is preferable to use it at a concentration within a range of from 20 to 50 wt %.

In the present invention, the hydrogenation sufficiently proceeds under 1 atm of hydrogen, because the catalyst has a very high activity. Taking account of economic merits, however, it should preferably be within a range of from 1 to 100 atm, or more preferably, from 3 to 50 atm. Considering economic merits for the process, it is possible to maintain a high activity even under a pressure of up to 10 atm.

The reaction temperature should preferably be within a range of from 15° to 100° C., while it is possible to cause the reaction at a temperature near the room temperature as within a range of from 25° to 40° C . However, the present invention is characterized in that the raction proceeds even at a low temperature of from −100° to 0° C. The reaction is completed in a period of time within a range of from a few minutes to ten hours, depending upon such reaction conditions as reaction substrate concentration, temperature and pressure.

The reaction system in the present invention may be in batch or continous.

Now, the method of the present invention is described in further detail below by means of examples.

In addition, the present invention relating to the method for producing an optically active alcohol provides also an embodiment wherein the above-mentioned asymmetric hydrogenation catalyst is a complex of a VIII-group metal, for example, a metal complex having an optically active ligand, one therein the base is a hydroxide or a salt of an alkali metal or an alkaline earth metal, or a quaternary ammonium salt, and one wherein the optically active compound as a nitrogen-containing asymmetric is a optically active amine compound.

An asymmetric hydrogenation catalyst can be expressed, for example, by the following general formula (5):

$$M^1 \, XmLn \qquad (5)$$

(where, M' is a VIII-group transition metal such as ruthenium, rhodium, iridium, palladium, or platinum; X is hydrogen, a halogen atom, a carboxyl group, a hydroxy group, or a alkoxy group; L is an optically active phosphine ligand or an optically active organic arsenic ligand; and m and n are integers), and the base may be a metal salt or a quaternary ammonium salt expressed by the following general formula (6):

(where, $M^2$ is an alkali metal or an alkaline earth metal; and Y is hydroxy group, alkoxy group, mercapto group or naphthyl group).

The carbonyl compound which is the raw material in the present invention is expressed by the general formula (2) In this case, $R^3$ is a non-substituted or substituted aromatic monocyclic or polycyclic hydrocarbon group, a saturated or unsaturated aliphatic or cyclic-hydrocarbon group, or a hetero-monocyclic or polycyclic group containing heteroatoms such as nitrogen, oxygen or sulfur atoms, and applicable ones include, for example, aromatic monocyclic or polycyclic groups such as phenyl group, 2-methylphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, 4-isopropylphenyl, 4-tert-butylphenyl, 4-vinylphenyl, cumenyl, mesityl, xylyl, 1-naphthyl, 2-naphthyl, anthryl, phenanthryl, and indenyl; and hetero-monocyclic or polycyclic groups and ferrocenyl group such as thienyl, furyl, pyranyl, xanthenyl, pyridyl, imidazolyl, indolyl, carbazolyl, and phenanthrolyl. $R^4$ is hydrogen, saturated or un-saturated hydrocarbon group, aryl group, or a functional group containing heteroatoms, and applicable ones include, for example, alkyl groups such as methyl, ethyl, propyl, butyl, pentyl, hexyl and heptyl; cycloalkyl groups such as cyclopropyl, cyclobutyl, cyclopentyl and cyclohexyl; and unsaturated hydrocarbon and other groups such as benzyl, vinyl and allyl. Furthermore, β-keto acid derivatives having a functional group at β-position are also applicable.

In case of cyclic group formed by conecting $R^3$ and $R^4$, for example, saturated or unsaturated cyclo-aliphatic groups providing cyclic ketone such as cyclopentanone, cyclohexanone, cycloheptanone, cyclopentenone, cyclohexenone, cycloheptenone; substituted saturated or unsaturated cyclo-aliphatic groups having substitution groups selected from alkyl, aryl, unsaturated alkyl, aliphatic or cyclo-aliphatic group containing hetero atom; are mentioned.

In the transition metal complex expressed by the general formula (5) in the present invention, $M^1$ is a VIII-group transition metal such as ruthenium, rhodium, iridium, palladium and platinum, and among others, ruthenium is particularly preferable. X is hydrogen, halogen atom, carboxyl group, hydroxyl group or alkoxy group. L is an optically active phosphine ligand or the like, and applicable ones include BINAP:2,2'-bis-(diphenylphosphino)-1,1'-binaphthyl, BINAP derivative having alkyl group or aryl group connected to naphthyl ring, such as H₈BINAP; BINAP derivative having 1–5 alkyl substitution group(s) at sito of aromatic ring on phosphorus atom, for example TolBINAP: 2,2'-bis-(di-p-tolylphosphino)-1,1'-binaphthyl, BICHEP: 2,2'-bis-(dicyclohexylphosphino)-6,6'-dimethyl-1,1'-biphenyl, BPPFA; 1-[1,2-bis(diphenylphosphino) ferrocenyl] ethyldimethylamine, CHIRAPHOS; 2,3-bis (diphenylphosphino) butane, CYCPHOS: 1-cyclohexyl-1,2-bis(diphenylphosphino)ethane, DEGPHOS: substitution-3, 4-bis(diphenylphosphino)pyrmethylolidine, DIOP: 2,3-0-isopropylidene-2,3-dihydroxy-1,4-bis(diphenyl-phosphino) butane, DIPAMP: 1,2-bis[(0-methoxy phenyl) phenylphosphino]ethane, DuPHOS: substitued-1,2-bis (phospholano) benzene, NORPHOS: 5,6-bis (diphenylphosphino)-2-norbornene, PNNP: N,N'-bis (diphenylphosphino)-N,N'-bis(1-phenylethyl) ethylenediamine, PROPHOS 1,2-bis(diphenylphosphino)

propane, and SKEWPHOS: 2,4-bis(diphenylphosphino) pentane. In addition, an optcally active phosphine ligand (an optically active phosphine ligand comprising substitution group having different group, or an optically active phosphine ligand of which at least one group is an optically active group) may be used. A bidentate phosphine ligand has an n of 1 or 2, and a monodentate phosphine ligand has an n of 3 or 4. It is needless to mention that the optically active phosphine ligand applicable in the present invention is not limited at all to these values, and the metal is not limited at all to ruthenium.

The amount of the VIII-group transition metal complex in the present invention, varying with the reactor, the reaction system and economic merits, can be at a ratio within a range of from 1/100 to 1/100,000 in mole ratio, or more preferably, within a range of from 1/600 to 1/10,000 in mole ratio relative to the carbonyl compound which is the reaction substrate.

In the base expressed by the general formula $M^2Y$ used in the present invention, $M^2$ is an alkali metal or an alkaline earth metal, and Y is hydroxy group, alkoxy group, mercapto group or naphthyl group, and more specifically, applicable ones include KOH, $KOCH_3$, $KOCH(CH_3)_2$, $KOC(CH_3)_3$, $KC_{10}H_8$, LiOH, $LiOH_3$, and $LiOCH(CR_3)_2$, NaOH, $NaOCH_3$, $NaOCH(CH_3)_2$, $NaOC(CH_3)_3$ as well as quaternary ammonium salt.

The consumption of the base as described above should be within a range of from 0.5 to 100 equivalents, or more preferably, from 2 to 40 equivalents relative to the VIII-group transition metal complex.

The nitrogen-containing compound such as an optical active amino compound used in the present invention may be an opically atctive monoamine in which at least one of the substitution groups is an optically active group and the remaining ones include hydrogen, or saturated or unsaturated hydrocarbon group or aryl group, or an optically active diamine compound expressed by the following general formula (7):

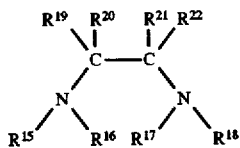

(where, $R^{15}$, $R^{16}$, $R^{17}$ and $R^{18}$ are hydrogen or saturated or unsaturated hydrocarbon group, aryl group, urethane group or sulfonyl group, and $R^{19}$, $R^{20}$, $R^{21}$ and $R^{22}$ are the same or different groups such that carbons bonded with these substitution groups form centers of asymmetricity, and represent hydrogen or alkyl group, aromatic monocyclic or polycyclic, saturated or unsaturated hydrocarbon group, and cyclic hydrocarbon group). Examples include such optically active diamine compounds as optically active 1,2-diphenylethylene diamine, 1,2-cyclohexanediamine, 1,2-cycloheptanediamine, 2,3- dimethylbutanediamine, 1-methyl-2,2-diphenyl ethylenediamine, 1-isobutyl-2,2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, 1-isopropyl-2,2-di(p-methoxyphenyl)ethylenediamine) 1-benzyl-2,2-di(p-methoxyphenyl)ethylenediamine, 1-methyl-2,2-dinaphthylethylenediamine, 1-isobutyl-2,2-dinaphthylethylenediamine, and 1-isopropyl-2,2-dinaphthyl-ethylenediamine, and optically active diamine, compounds in which one or both of the substitution groups $R^{15}$ and $R^{17}$ are sulfonyl group or urethane group. Optically active diamine compounds are not limited to the optically active ethylene-diamine derivatives enumerated above, but include also optically active propanediamine, butanediamine and phenylenediamine derivatives. The amount of these optically active amine compounds should be within a range of from 1 to 10 equivalents relative to the transition metal complex in the case of a monoamine compound, or more preferably, from 2 to 4 equivalents, and within a range of from 0.6 to 2.5 equivalents in the case of a diamine compound, or more preferably, from 1 to 2 equivalents.

In the present invention, it is important, in order to obtain a high optical yield, to achieve an appropriate combination of an absolute configuration of the optically active ligand and the absolute configuration of the optical active nitrogen-containing compound in the asymmetric hydrogenation catalyst as the catalyst component. The combination of S-phosphine ligand and S,S-diamine is, for example, best choice and gives (R)— alcohol. The combination of S-phosphine ligand and R,R-diamine, while the reaction proceeds, results in an extremely low optical yield.

The optical active transition metal complex, the base and the optical active nitrogen-containing compound used as catalyst component in the present invention as described above are indispensable for achieving a high optical yield. Lack of even any of these constituents makes it impossible to obtain alcohol with a sufficient optical activity and a high purity.

In the present invention, furthermore, any liquid solvent which can dissolve the reaction raw materials and catalyst components may be used. Applicable solvents include aromatic hydrocarbon solvents such as toluene and xylene, aliphatic hydrocarbon solvents such as pentane and hexane, halogen-containing hydrocarbon solvents such as methylene chloride, diethyl ether type solvents such as ether and tetrahydrofuran, alcohol type solvents such as methanol, ethanol, 2-propanol, butanol, benzyl alcohol, and organic solvents containing heteroatoms such as acetonitrile, DMF and DMSO. Since the product is alcohol, alcohol type solvents are preferable. More preferably, 2-propanol may be preferably used. When the reaction substrate is hardly soluble in a solvent, a mixed solvent comprising ones selected from those enumerated above may be used.

The amount of solvent is determined from solubility of the reaction substrate and relative economic merits. In the case of 2-propanol, the reaction may be caused at a substrate concentration within a range of from a low concentration of under 1% to a state near the non-existence of solvent, but it is preferable to use it at a concentration within a range of from 20 to 50 wt. %

In the present invention, the hydrogenation sufficiently proceeds under 1 atm of hydrogen because the catalyst has a very high activity. Taking account of economic merits, however, it should preferably be within a range of from 1 to 100 atm, or more preferably, from 3 to 50 atm. Considering economic merits for the process as a whole, it is possible to maintain a high activity even under a pressure of up to 10 atm.

The reaction temperature should preferably be within a range of from 15° to 100° C., while it is possible to cause the reaction at a temperature near the room temperature as within a range of from 25° to 40° C. However, the present invention is characterized in that the reaction proceeds even at a low temperature of from −100° to 0° C. The reaction is completed in a period of time within a range of from a few minutes to ten hours, depending upon such reaction conditions as reaction substrate concentration, temperature and pressure. Now, the present invention is described in detail by means of examples.

The form of reaction in the present invention may be in batch or continuous.

EXAMPLES

Example 1

$RuCl_2[P(C_6H_5)_3]_3$(9.6 mg, 0.01 mmol), KOH(0.02 mmol), ethylenediamine (0.01 mmol) and acetophenone (60 mg. 5.0 mmol) were dissolved into 3 ml of 2-propanol, and after deaeration for argon substitution, the resultant mixture was totally transferred into a glass autoclave of 100 ml. Then, hydrogen was charged into it until a prescribed pressure (3 atm) was achieved and reaction was started. After stirring the reaction mixture for 30 minutes, the reaction pressure was brought back to the atmospheric pressure. Phenethylalcohol was identified as the reaction product by gas chromatography and NMR analysis of the reaction mixure, and the product was quantitatively measured. The reaction substrate was totally consumed, giving a phenethyl alcohol yield as the product of over 99%.

Examples 2 to 23

Uner the conditions shown in Example 1, with a reaction substrate changed from acetophenone, hydrogenation was conducted, and a corresponding alcohol compound was obtained substantially in a theoretical amount in each of these Examples. The raw material carbonyl compounds and the yields of the resultant compounds are shown in Table 1 to 3.

TABLE 1

| Example No. | (Reaction substrate) Raw material carbonyl compound | Product alcohol yield (%) |
|---|---|---|
| 1 | (phenyl-C(=O)-CH3) | 99 |
| 2 | (2-methylphenyl-C(=O)-CH3) | 95 |
| 3 | (3-methylphenyl-C(=O)-CH3) | 99 |
| 4 | (2-CH3O-phenyl-C(=O)-CH3) | 50 |
| 5 | (3-CH3O-phenyl-C(=O)-CH3) | 99 |
| 6 | (4-CH3O-phenyl-C(=O)-CH3) | 99 |

TABLE 1-continued

| Example No. | (Reaction substrate) Raw material carbonyl compound | Product alcohol yield (%) |
|---|---|---|
| 7 | (2-Cl-phenyl-C(=O)-CH3) | 70 |

TABLE 2

| Example No. | (Reaction substrate) Raw material carbonyl compound | Product alcohol yield (%) |
|---|---|---|
| 8 | (3-Cl-phenyl-C(=O)-CH3) | 98 |
| 9 | (4-Cl-phenyl-C(=O)-CH3) | 99 |
| 10 | (phenyl-C(=O)-C3H7) | 98 |
| 11 | (phenyl-C(=O)-CH(CH3)2) | 99 |
| 12 | (phenyl-C(=O)-(CH2)n-C(=O)-OC2H5), n = 2–5 | 50 |
| 13 | (2-naphthyl-C(=O)-CH3) | 99 |
| 14 | (1-naphthyl-C(=O)-CH3) | 99 |

TABLE 2-continued

| Example No. | (Reaction substrate) Raw material carbonyl compound | Product alcohol yield (%) |
|---|---|---|
| 15 | [structure: 2-acetylfluorene] | 98 |

TABLE 3

| Example No. | (Reaction substrate) Raw material carbonyl compound | Product alcohol yield (%) |
|---|---|---|
| 16 | [structure: acetylphenanthrene] | 98 |
| 17 | [structure: 4-acetylbiphenyl] | 99 |
| 18 | [structure: acetylferrocene] | 97 |

TABLE 3-continued

| Example No. | (Reaction substrate) Raw material carbonyl compound | Product alcohol yield (%) |
|---|---|---|
| 19 | [structure: 3-acetylpyridine] | 97 |
| 20 | [structure: phenylacetone] | 99 |
| 21 | [structure: α-tetralone] | 99 |
| 22 | [structure: cyclohexyl methyl ketone] | 98 |
| 23 | [structure: 2-heptanone] | 99 |

Example 24–30

Under the conditions shown in Example 1, hydrogenation reaction using unsaturated carbonyl compounds having the carbon—carbon double bond or the carbon—carbon triple bond. Corresponding alcohol compounds were obtained at high yields.

Carbon—carbon multiple bonds were not hydrogenated, and cabonyl groups only were hydrogenated. The result of above reaction are shown in Table 4.

TABLE 4

| Example No. | Reaction substrate Raw material carbonyl compound | Product alcohol yield (%) |
|---|---|---|
| 24 | [structure: benzalacetone / cinnamaldehyde derivative] | 95 |
| 25 | [structure: 3-methylcyclohex-2-enone] | 98 |

TABLE 4-continued

| Example No. | Reaction substrate Raw material carbonyl compound | Product alcohol yield (%) |
|---|---|---|
| 26 | 4-(1-butynyl)acetophenone structure | 98 |
| 27 | dec-9-enyl methyl ketone structure | 95 |
| 28 | benzaldehyde structure | 95 |
| 29 | decanal structure | 95 |
| 30 | (E)-2-tridecenal structure | 88 |

Example 31–39

Under the conditions shown in Example 1, with 4-methylcyclohexynone and 2-phenylmethylketone having chiral carbon atom group in molecular structure, the effect of added phosphine ligands were surveyed.

Each reaction provides quantitatively alcohol products. The resultant cis/trans ratio of alcohols derived from 4-methylcyclohexanone and syn/anti ratio of alcohol derived from 2-phenylmethylketone were shown in Table 5.

TABLE 5

| Example No. | Phosphine ligand | 4-methylcyclohexanone cis:trans | 2-phenylmethylketone syn:anti |
|---|---|---|---|
| 31 | $PPh_3$ | 92:8 | 14:86 |
| 32 | $P(C_6H_4\text{-}F)_3$ | 93:7 | 22:78 |
| 33 | $P(o\text{-}C_6H_4\text{-}CH_3)_3$ | 92:8 | 6:94 |
| 34 | $P(p\text{-}C_6H_4\text{-}CH_3)_3$ | 92:8 | 5:95 |

TABLE 5-continued

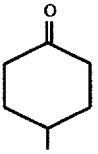

| Example No. | Phosphine ligand | cis:trans | syn:anti |
|---|---|---|---|
| 35 | 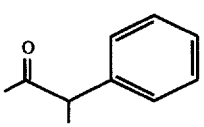 | 93:7 | 4:96 |
| 36 | dppe | 70:30 | 24:76 |
| 37 | dppp | 74:26 | 15:85 |
| 38 | dppb | 88:12 | 8:92 |
| 39 | 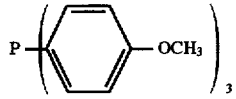 | 82:18 | 24:76 |

Example 40

To prove the high activity of the catalyst of the present invention, the ratio of the reaction substrate to the catalyst was set to 5,000 and reaction was caused to determine the initial reaction rate.

More specifically, acetophenone (20 mol), $RuCl_2[P(C_6H_5)_3]_3$ (3.8 mg, 0.004 mol), KOH (0.08 mol) and ethylenediamine (0.004 mol) were dissolved into 12 ml 2-propanol, and after deaeration and substitution with argon gas, the resultant mixture was totally transferred to a 500 ml glass autoclave. Hydrogen was then injected to a prescribed pressure (3 atm) and reaction was started. The reaction was caused by direct connection to a hydrogen cylinder so as to keep a constant hydrogen pressure. The reaction was completed in 80 minutes, and the initial rate of the reaction was determined to be 6,700 mol/Ru catalyst mol. hr.

Example 41

Reaction was conducted under the same condition as in Example 1 except for a hydrogen pressure of 1 atom. The initial rate was 880 mol/Ru catalyst mol.hr.

Example 42

Reaction was conducted under the same conditions as in Example 1 except for a hydrogen pressure of 50 atom. The initial rate was 23, 000 mol/Ru catalyst mol. hr.

Example 43

Reaction was conducted under the same conditions as in Example 1 except for a reaction temperature of –20° C. The reaction was completed in ten hours and phenethylalcohol was obtained at a yield of 98%.

Comparative Example 1

Reaction was conducted under the same conditions as in Example 1 except that KOH and ethylene diamine were not added. The reaction rate was 5 mol/Ru catalyst mol. hr., and the reaction showed almost no progress.

Comparative Example 2

Reaction was conducted under the same conditions as in Example 1, but without adding ethylenediamine. The reaction rate was 70 mol/Ru catalyst mol. hr. oven in the absence of hydrogen.

Comparative Example 3

Reaction was conducted under the same conditions as in Example 1, but without adding KOH. The reaction rate was 5 mol/Ru catalyst mol.hr., and the reaction showed almost no progress.

Comparative Example 4

Reaction was conducted under the same conditions as in Example 1, but without injecting hydrogen. The reaction rate was 8 mol/Ru catalyst mol.hr., and the reaction showed almost no progress.

Example 44

Reaction was caused under the same conditions as in Example 1 except for the use of p-diacetylbenzene as a carbonyl compound. This gave p-bis(1-hydroxy)benzene was obtained at a yield of 99%.

According to the present invention, as described above in detail, it is possible to manufacture alcohol from a carbonyl compound efficiently at a high yield.

Following examples show the present invention for producing optically active alcohols.

The applicable reaction substrates, optically active phosphines and diamine ligands as typical examples are shown in Table 6, and Table 7.

TABLE 6
Carbonyl compound
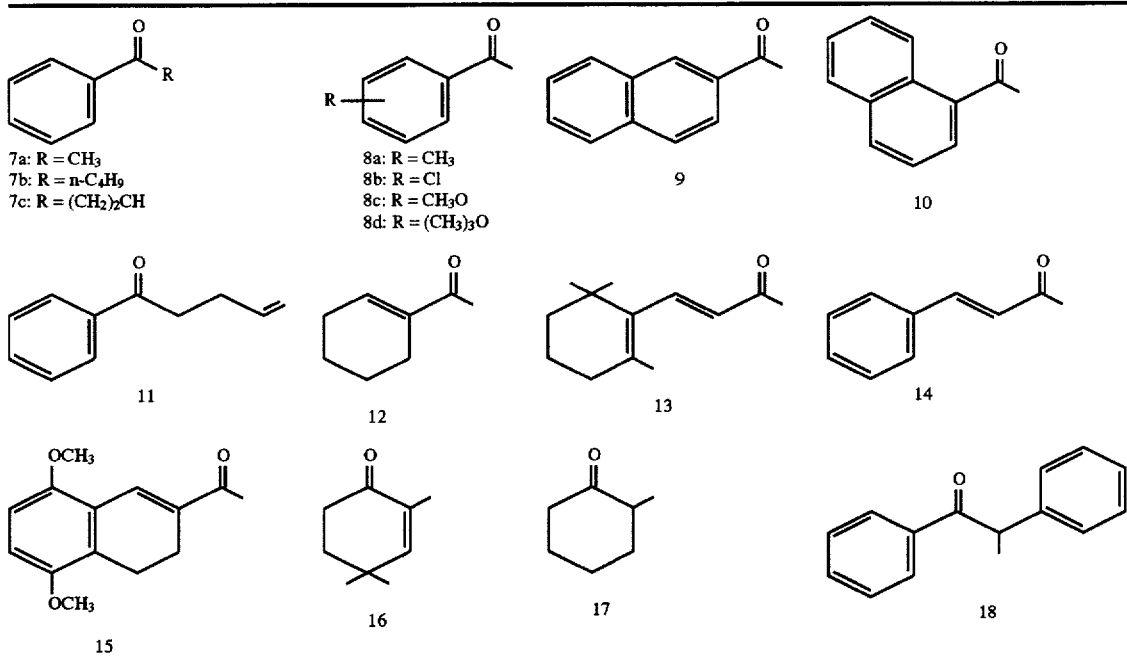
TABLE 7
Phasphine ligands
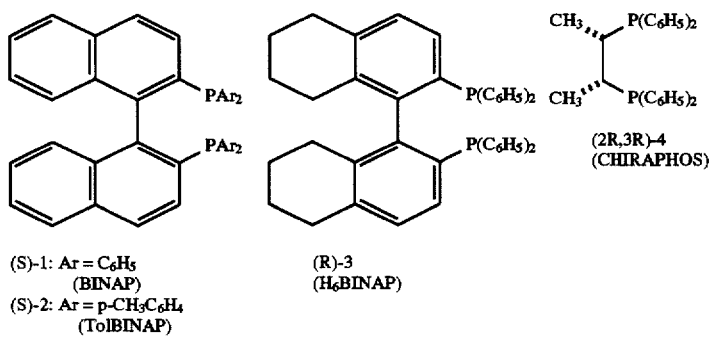
(S)-1: Ar = C$_6$H$_5$ (BINAP)
(S)-2: Ar = p-CH$_3$C$_6$H$_4$ (TolBINAP)
(R)-3 (H$_6$BINAP)
(2R,3R)-4 (CHIRAPHOS)
Diamine ligand
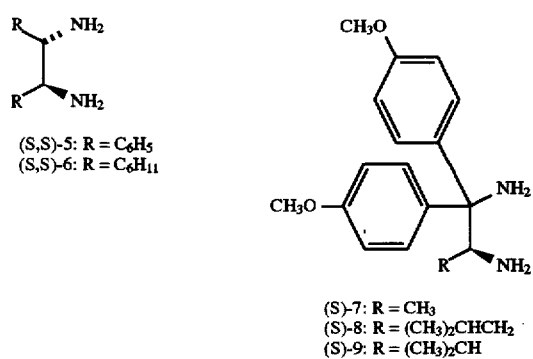
(S,S)-5: R = C$_6$H$_5$
(S,S)-6: R = C$_6$H$_{11}$
(S)-7: R = CH$_3$
(S)-8: R = (CH$_3$)$_2$CHCH$_2$
(S)-9: R = (CH$_3$)$_2$CH

Example 45

Into a Schlenk reaction tube, 0.5M 2-propanol solution (40 µL) of KOH, (S,S)-diphenylethylenediamine (2.1 mg, 0.01 mol), 1'-actonaphthone (Compound 10 in Table 6)(85 mg, 5.0 mol) and 3 ml 2-propanol were charged in an argon gas flow. After deaeration and argon substitution, the reaction solution was adjusted by adding $RuCl_2((S)\text{-binap})$ $(dmf)_n$ (9.6 mg, 0.01 mol). This solution was repeatedly subjected to deaeration and argon substitution to achieve complete dissolution, and then, the reaction was started by transferring the solution into a 100 ml glass autoclave and injecting hydrogen into it to a prescribed pressure. After stirring for six hours at 28° C., temperature was brought to the room temperature, and the reaction product was subjected to gas chromatography and, H NMR analysis to identify the product and determine reaction yield (higher than 99%). Further, the optical purity of the resultant (R)-1-(1-naphthyl)-ethanol was determined by means of an optically active column from HPLC, the result being 97% ee.

Examples 46 to 58

In the same manner as in Example 45, the reaction was caused under the reaction conditions including optically active diamine, hydrogen pressure, temperature and reaction type with the carbonyl compounds as shown in Table 6 as the reaction substrates, and respective optically active alcohol products were obtained with high yields. The results are shown in Table 8.

Example 59

In the same manner as in Example 1, p-diacetylbenzene was used as the reaction substrate, and (S)-isopropyl-2,2-di(p-methoxyphenyl)ethylenediamine was used as the optically active diamine. Reaction was caused under a hydrogen pressure of 4 atm at 28° C. for 1.5 hours. The resultant diol had a ratio of optically active compound to meso compound of 85:15 and the optical active material had an optical purity of over 99%.

Example 60

Reaction was caused in a scale increased to 35 times as large as that of Example 1. From 30 g 1'-acetonaphthone (Compound 10 in Table 1), (R)-1-(1-naphthyl)ethanol was obtained in an amount of 27.90 g. The reaction product was separated by vacuum distillation (98°–101° C./0.5 mmHg), and a pure product of an optical purity of 96% was obtained.

Comparative Example 5

Reaction was carrier out under the same conditions as in Example 1, using ethylene diamine in place of (S,S)-diamine. Corresponding optically active alcohol was obtained with an optical purity of 57%.

Example 61–66

Under same conditions shown in Example 45, hydrogenation reactions were carried by using unsaturated carbonyl compounds having the carbon—carbon double bonds in each molecular structure as raw materials. Corresponding optically active alcohols were obtained at high yield. Carbon—carbon multiple bonds were not hydrogenated and carbonyl groups only were hydrogenated. The results are shown in above Table 8.

Example 67

Under the same condition of the Example 45, hydrogenation was conducted by using a unsaturated cyclicketone (Compound No. 16 shown in Table 6)(0.35 g, 2.5 mmol), and corresponding optically active unsaturated alcohol was quantitatively obtained. As shown in Table 8, optical purity was 93% ee.

Example 68

Under the same condition except addition of KOH of 0.2 mmol(0.4M, 2-propanol solution 444 µl), racemic 2-methyl cyclohexanone (compound No. 17, shown in Table 6, (0.57 g, 5.0 mmol) was hydrogenated. The reaction provides optical active alcohol having cis/trans ratio of 97.7:2.3 by

TABLE 8

| | Carbonyl | Photoactive ligand | | Reaction condition | | | Product | | |
|---|---|---|---|---|---|---|---|---|---|
| Example | compound | Phosphine | Diamine | $H_2$ atm. | Temp. °C. | Time, h | % yield | % ee | confign |
| 46 | 7a | (S)-1 | (S)-8 | 4 | 28 | 3 | >99 | 87 | R |
| 47 | 7b | (S)-1 | (S)-7 | 4 | 28 | 3 | >99 | 90 | R |
| 48 | 7c | (S)-2 | (S)-9 | 8 | 28 | 6 | >99 | 95 | R |
| 49 | o-8a | (S)-2 | (S, S)-5 | 4 | 28 | 5 | >99 | 94 | R |
| 50 | p-8a | (R)-1 | (R)-9 | 4 | 28 | 3 | >99 | 91 | S |
| 51 | o-8b | (S)-2 | (S, S)-5 | 50 | 28 | 3 | >99 | 94 | R |
| 52 | m-8b | (S)-2 | (S)-9 | 8 | 28 | 1 | 96 | 90 | R |
| 53 | p-8b | (S)-2 | (S)-9 | 8 | 28 | 16 | >99 | 94 | R |
| 54 | m-8c | (R)-1 | (R)-9 | 8 | 30 | 3 | 99 | 88 | S |
| 55 | p-8c | (R)-1 | (R)-9 | 4 | 28 | 3 | >99 | 92 | S |
| 56 | p-8d | (S)-2 | (S, S)-5 | 4 | 24 | 1.5 | >99 | 96 | R |
| 57 | 9 | (S)-2 | (S)-9 | 1 | 26 | 18 | 99 | 95 | R |
| 58 | 9 | (S)-2 | (S)-9 | 50 | −22 | 3 | 98 | 97 | R |
| 61 | 11 | (S)-1 | (S)-9 | 8 | 28 | 3 | 97 | 90 | R |
| 62 | 12 | (S)-1 | (S)-9 | 8 | 28 | 5 | 91 | 98 | R |
| 63 | 13 | (R)-1 | (R, R)-6 | 8 | −20 | 20 | 95 | 92 | S |
| 64 | 13 | (2R, 3R)-4 | (S, S)-5 | 4 | 28 | 19 | >99 | 53 | S |
| 65 | 14 | (R)-3 | (S)-7 | 4 | 28 | 1 | >99 | 69 | S |
| 66 | 15 | (R)-1 | (R)-9 | 8 | 28 | 1.5 | 100 | 94 | S |
| 67 | 16 | (S)-1 | (R)-5 | 8 | 28 | 2 | 100 | 93 | R |
| 68 | 17 | (S)-1 | (R)-6 | 8 | 28 | 2.5 | 100 | 80 | (cis) |
| 69 | 18 | (S)-1 | (S)-9 | 8 | 28 | 20 | 96 | 91 | (1R, 2R) | procedure of dynamic kinetic resolution at site of 2-asymmetric carbon.

As shown in Table 8, optical purity of cis form was 80% ee.

Example 69

Under same condition of Example 68, racemic compound (No. 18, shown in Table 6) (1.05 g, 5 mmol) was hydrogenated.

The reaction was carried out though dynamic kinetic resolution, and provides optically active alcohol having anti/sym ratio of 97.0:3.0.

As shown in Table 8, optical purity of anti-form was 91% ee.

What is claimed is:

1. A method for producing an alcohol, which comprises reacting a carbonyl compound with molecular hydrogen ($H_2$) in the presence of a homogeneous hydrogenation catalyst, a base and a diamine compound, said homogeneous hydrogenation catalyst being a ruthenium-phosphine ligand complex, and said base being a hydroxide of salt or an alkali metal or an alkaline earth metal or quaternary ammonium salt.

2. The method as claimed in claim 1, wherein said carbonyl compound is represented by the following formula:

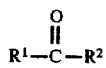

where $R^1$ and $R^2$ are hydrogen, phenyl, 2-methylphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, cumenyl, mesityl, xylyl, 1-naphthyl, 2-naphthyl, anthryl, phenanthryl, indenyl, thienyl, furyl, pyranyl, xanthenyl, pyridyl, pyrrolidyl, imidazolyl, indolyl, phenanthroylyl, ferrocenyl, methyl, ethyl, propyl, butyl, pentyl, hexyl, heptyl, cyclopropyl, cyclobutyl, cyclopentyl and cyclohexyl, benzyl, vinyl or allyl, or the following ketones which may be substituted or unsubstituted; cyclopentanone, cyclohexanone, cycloheptanone, cyclopentenone, cyclohexenone, cycloheptenone.

3. The method according to claim 1, wherein the diamine is represented by the formula $R^{11}R^{12}N$—Z—$NR^{13}R^{14}$, wherein $R^{11}$, $R^{12}$, $R^{13}$ and $R^{14}$ represent hydrogen or the same or different members selected from the group consisting C1–C10 alkyl, cycloalkyl and aryl, or is a cyclic diamine, and Z is C1–C6 alkyl, cycloalkyl or aryl.

4. A method for producing an optically active alcohol, which comprises the step of subjecting a carbonyl compound expressed by the following formula:

where $R^3$ is phenyl 2-methylphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3chlorophenyl, 3-vinylphenyl, 4-methylphenyl, 4-ethylphenyl, 4-isopropylphenyl, 4-tert-butylphenyl, 4-vinylphenyl, cumenyl, mesityl, xylyl, 1-naphthyl, 2-naphthyl, anthryl, phenanthryl, indenyl, ferrocenyl, thienyl, furyl, pyranyl, xanthenyl, pyridyl, imidazolyl, indolyl, carbazolyl, or phenanthrolyl, and $R^4$ is hydrogen, methyl, ethyl, propyl, butyl, pentyl, hexyl, heptyl, cyclopropyl, cyclobutyl, cyclopentyl, cyclohexyl, benzyl, vinyl or allyl, or the following cyclic ketones which may be substituted or unsubstituted; cyclopentanone, cyclohexanone, cycloheptanone, cyclopentenone, cyclohexenone, cycloheptenone, to a hydrogenation reaction with molecular hydrogen ($H_2$) in the presence of an asymmetric hydrogenation catalyst of a transition metal, a base and an optically active diamine compound, thereby producing an optically active alcohol expressed by the following formula:

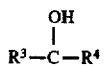

where $R^3$ and $R^4$ are the same groups as above, or the cyclic alcohols corresponding to the above cyclic ketones, said asymmetric hydrogenation catalyst being a ruthenium-optically active phosphine ligand complex, and said base being a hydroxide or salt of an alkali metal or an alkaline earth metal, or a quaternary ammonium salt.

5. The method according to claim 4, wherein the optically active diamine compound is, 1,2-diphenylethylene diamine, 1,2- cyclohexanediamine, 1,2-cycloheptanediamine, 2,3-dimethylbutanediamine, 1-methyl-2,2-diphenyl ethylenediamine, 1-isobutyl-2,2-diphenylethylenediamine, 1-isopropyl-2,2-diphenylethylenediamine, 1- methyl-2,2-di (p-methoxyphenyl)ethylenediamine, 1-isobutyl-2,2-di(p-methoxyphenyl)ethylenediamine, 1-isopropyl-2,2-di(p-methoxyphenyl)ethylenediamine, 1-benzyl-2,2-di(p-methoxyphenyl)ethylenediamine, 1-methyl-2,2-dinaphthylethylenediamine, 1-isobutyl-2,2-dinaphthylethylenediamine, 1-isopropyl-2,2-dinaphthylethylenediamine, propane diamine, butanediamine or phenylenediamine, and wherein each amine of said diamine may be substituted by a sulfonyl or urethane group.

* * * * *